(12) United States Patent
Prestegard et al.

(10) Patent No.: US 7,146,277 B2
(45) Date of Patent: Dec. 5, 2006

(54) NMR ASSISTED DESIGN OF HIGH AFFINITY LIGANDS FOR STRUCTURALLY UNCHARACTERIZED PROTEINS

(75) Inventors: James H. Prestegard, 1071 Scotland Bend Ct., Watkinsville, GA (US) 30677; Nitin U. Jain, Athens, GA (US); Hashim M. Al-Hashimi, Athens, GA (US); Laura C. Morris, Auburn, GA (US); Andre P. Venot, Athens, GA (US)

(73) Assignee: James H. Prestegard, Athens, GA (US)

( * ) Notice: Subject to any disclaimer, the term of this patent is extended or adjusted under 35 U.S.C. 154(b) by 709 days.

(21) Appl. No.: 09/880,648

(22) Filed: Jun. 13, 2001

(65) Prior Publication Data

US 2002/0042150 A1  Apr. 11, 2002

Related U.S. Application Data

(60) Provisional application No. 60/211,057, filed on Jun. 13, 2000.

(51) Int. Cl.
*G06F 19/00* (2006.01)
*G01F 1/716* (2006.01)
*A61B 5/055* (2006.01)

(52) U.S. Cl. ........................ 702/19; 505/844
(58) Field of Classification Search ................ 702/19, 702/20; 436/501
See application file for complete search history.

(56) References Cited

U.S. PATENT DOCUMENTS

| 5,698,401 | A | 12/1997 | Fesik et al. |
| 5,804,390 | A | 9/1998 | Fesik et al. |
| 5,891,643 | A | 4/1999 | Fesik et al. |
| 5,989,827 | A | 11/1999 | Fesik et al. |
| 6,027,941 | A | 2/2000 | Jarvie et al. |
| 6,043,024 | A | 3/2000 | Fesik et al. |

OTHER PUBLICATIONS

Fischer et al. (Biochemistry (1999) vol. 38, pp. 9013-9022).*
Bolon et al., "Residual Dipolar Coupling Derived Orientational Constraints on Ligand Geometry in 53 kDa Protein-Ligand Complex," *J. Mol. Biol. 1999*, 293, 107-115.
Henrichsen et al., "Bioaffinity NMR Spectroscopy: Identification of an E-Selectin Antagonist in a Substance Mixture by Transfer NOE," *Agnew. Chem. Int. Ed.* 1999, 38 (1/2), 98-102.
Jahnke et al., "Second-Site NMR Screening with a Spin-Labeled First Ligand," *J. Am. Chem. Soc.* 2000, 122, 7394-7395.
Johnson et al., "The Cellulose-binding Domains from *Cellulomonas fimi* β-1,4-Glucanase CenC Bind Nitroxide Spin-labeled Cellooligosaccharides in Multiple Orentiations," *J. Mol. Biol.* 1999, 287, 609-625.
Koenig et al., "Measurement of dipolar couplings in a transducin peptide fragment weakly bound to oriented photo-activated rhodopsin," *Journal of Biomolecular NMR.* 2000, 16, 121-125.

* cited by examiner

*Primary Examiner*—Marjorie A. Moran
*Assistant Examiner*—Lori A. Clow
(74) *Attorney, Agent, or Firm*—Clark G. Sullivan; King & Spalding LLP (57) ABSTRACT

Methods of using NMR spectroscopy for identifying ligands that bind to structurally uncharacterized proteins, and improving the binding affinity of ligands for biological targets are disclosed. One aspect of the method includes preparing first NMR spectra of a first complex comprising the biological target and a paramagnetically labeled derivative of a first ligand, preparing a second NMR spectra of a second complex comprising the biological target and a second ligand, and analyzing the spectra to determine whether the second ligand binds to the biological target within the paramagnetic zone of the paramagnetically labeled derivative. The first and second steps may be performed simultaneously, consecutively, or in any order.

17 Claims, 7 Drawing Sheets

* TEMPO synthesis contamination

The Orientational Parameters of AMM

Figure 7 13C-coupled proton spectrum of the UDP:GnT-V complex showing the couplings in the C1'-H1' anomeric region

Figure 8 Sauson-Flaumsteed projection of the directions of highest order of UDP:GnT-V complex

NMR ASSISTED DESIGN OF HIGH AFFINITY LIGANDS FOR STRUCTURALLY UNCHARACTERIZED PROTEINS

RELATED APPLICATIONS

This application claims priority under 35 U.S.C. § 119(e) to U.S. Provisional Application No. 60/211,057, filed Jun. 13, 2000.

GOVERNMENT SUPPORT

This invention was developed under the sponsorship of Grant No. GM33225 from the National Institutes of Health. The United States government has certain rights in this invention.

FIELD OF THE INVENTION

The present invention relates to methods for using NMR spectral analysis and paramagnetic labeling to design ligands having optimal 3-dimensional configurations for binding to a biological target.

BACKGROUND OF THE INVENTION

The past several decades have seen tremendous advances in our understanding of biological processes, and the rational design of pharmaceutical drugs based upon knowledge of those processes. Much effort has been devoted to identifying natural and synthetic ligands capable of interacting with proteins involved in biological processes. The recognition domains of proteins control biological processes in many ways, including: serving as loci of catalytic activity; allostearically regulating enzymatic activity; mediating signal transduction; effecting transport of cellular components; activating factors involved in transcribing or translating nucleic acids; and many others.

Drug discovery today typically follows the following sequence: (1) an active molecule is identified and compared to other molecules that have or do not have relevant biological activity; (2) based upon structure/activity relationships between the molecules, a chemist designs and prepares a library of potentially active molecules, often using combinatorial techniques; (3) the molecular biologist screens the library of molecules for relevant biological activity; (4) based upon the results of this screen, the chemist might prepare another library of compounds for testing. This process is repeated until several lead compounds are identified for more detailed investigation.

The foregoing method has led to the discovery of many important drugs. However, even high volume combinatorial chemistry and biological screening methods have proven no match for the complexity of protein structures and protein/ligand interactions involved in various biological mechanisms. A molecule might exhibit a relevant biological property in vitro, which scientists would attribute to ligand binding to a relevant protein. However, if the synthetic ligand does not sufficiently mimic the natural ligand, it can do more harm than good by affecting biological processes that are unrelated to the disease state being treated. In addition, if the synthetic ligand does not bind to the protein with sufficient affinity, it will not regulate the protein's activity sufficiently to control the targeted biological process.

The complexity of proteins greatly inhibits our ability to design custom synthetic ligands. Protein recognition domains often consist of multiple binding sites spread over different regions of the protein. Moreover, because the binding sites on proteins have specific three dimensional conformations, binding components of a ligand must be properly oriented to match the protein binding sites to have the appropriate effect. Variations in noncovalent interactions between ligands and proteins, such as the balance between Van der Waals and electrostatic interactions, further complicate the ability to design a synthetic ligand for a protein.

Efforts have been made recently to use NMR to improve the binding affinity of known ligands, by screening for other ligands that bind a protein near the protein binding site for the known ligand. Once a suitable second ligand is identified, the ligands are covalently linked to construct a hybrid ligand having greater binding affinity for the protein than either of the constituent ligands. A series of patents to Fesik et al., U.S. Pat. Nos. 5,698,401; 5,804,391; 5,891,643; 5,989,827; and 6,043,024 ("the Fesik patents") disclose such efforts, through a technique known as "SAR by NMR."

SAR by NMR uses a very sensitive two dimensional NMR experiment, a heteronuclear single quantum coherence (HSQC) experiment, to screen compound libraries for components that bind to protein targets, and uses a mapping of perturbed peaks to points in a three dimensional protein structure from the HSQC experiment to locate sites of binding on a protein surface. The experiment relies on uniform $^{15}N$ enrichment of the protein target and collection of peaks that correlate the $^{1}H$ and $^{15}N$ chemical shifts of directly bonded $^{15}N$—$^{1}H$ pairs that occur primarily in backbone amide bonds of the protein, one pair per residue. Effects on the chemical shifts of peaks coming from amide pairs on binding of drug components is largely restricted to proximate residues, and thus provides qualitative information on the location of the binding site for any one component. If the peaks can be assigned to specific amino acids and if the protein structure is known, the binding site can be spatially localized. When more than one interacting component can be localized, components binding to proximal sites can be assembled synthetically to achieve binding affinities that approximate the product of the individual component affinities. Thus, compounds that individually fail as drug leads because of low binding affinities can be combined to produce viable leads.

The SAR approach, while successful, is limited. The procedure does require assignment of peaks to the amino acid sequence of the protein, and it does require knowledge of the three dimensional structure of the protein. It is also often the case that additional experiments involving nuclear Overhauser effects (NOEs) between protons on a binding component and protons on the protein are needed to restrict possible orientations of each binding component relative to the protein surface and better define the relative geometries of components to be linked synthetically. Thus, even though the basic HSQC screen experiment is highly efficient, the additional experiments needed for assignment and structure determination are very time consuming. They also begin to fail when proteins become large. Work to date has been restricted to proteins that are less than 40 kDa in molecular weight and soluble to levels approaching 0.5 mM.

SAR by NMR is further limited by the intrinsic limitations of nuclear Overhauser effects. For example, to observe NOEs between a ligand and a protein in a complex, the NMR observable protons on the ligand must be sufficiently close to NMR observable protons on the protein surface for NOEs to be measured (typically within 5 Å). NOEs also rarely are used to characterize some types of complexes, for example oligosaccharide-protein complexes. In the latter case it is difficult to characterize interactions because the hydrogen-bonding networks involving hydroxyl proteins on the sugars are often part of the interface between protein and oligosaccharide. The hydroxyl protons are then the bulk of ones within 5 Å of protein protons, but they exchange rapidly with protons in bulk water making their NMR resonances hard to observe.

Therefore, it is an object of this invention to provide a method of identifying two or more ligands that bind to a protein recognition domain without assigning NMR peaks to the amino acid sequence of the protein, or characterizing the 3-D structure of the recognition domain.

It is another object of the invention to estimate the distance between ligand binding sites of the identified ligands on the surface of the protein.

It is another object of the invention to identify two or more ligands that bind to a biological target, and to covalently link the ligands at a bond length that approximates the distance of separation between the ligands when bound to a biological target, to thereby produce hybrid ligands having improved binding affinity for the biological target.

It is still another object of the invention to ascertain three dimensional orientations of ligands when bound to a biological target, and to combine the orientational information with distance information to produce hybrid ligands having even greater binding affinity for a biological target.

It is a further object of this invention to provide methods for characterizing ligand/protein interactions not susceptible to characterization by NOEs and other traditional NMR methods.

SUMMARY OF THE INVENTION

The invention is a new process that will lead to the identification and geometrical placement of ligands that are potential bioactive compounds (therapeutics), which can subsequently be chemically linked to produce new higher affinity ligands for proteins and other bioactive compounds. The strategy utilizes novel NMR methods for the search and placement of ligands. In a first step a known inhibitor, substrate, or analog thereof (first ligand), is linked chemically to a spin relaxation enhancement element such as a paramagnetic nitroxide spin-label or metal chelate. The distance-dependent relaxation enhancement of nuclear spins in the vicinity of the bound, labeled, ligand is then used to identify sites on the biological target, or on a second bound ligand directly, that are at appropriate distances for chemical linkage. In the case where protein sites are identified, these are detected via NMR resonances from the protein, and perturbations of the positions of these resonances is used in a screening procedure to identify a second ligand. In the case where sites on a second ligand are to be directly identified, the screening procedure uses relaxation enhancement (line broadening) of resonances for a potential second ligand, due to the presence of the first, labeled, ligand, as a screening procedure.

In a second step, residual dipolar couplings of magnetic nuclei are used to deduce relative orientations of the two ligands. Novel media that selectively impart orientational order to the biological target in the presence of a magnetic field are used to enhance the sensitivity of measured dipolar couplings. These media can be aqueous dispersions of lipid bicelles altered to have complementary charges to the protein target, aqueous dispersions of bateriophage that have been engineered to carry a domain of the target protein in their coats, or combinations of the above. Knowing not just the approximate separation of the component ligands (from step one), but also their relative orientations (from step two), greatly restricts the options for chemical linkage that must be explored. The successful linkage of two ligands can produce a compound with a binding constant that is approximately the product of the binding constants for the individual ligands.

Thus, the invention provides a method for (1) discovering multiple ligands that bind to the recognition domain of a protein or other biological target, and (2) covalently linking the ligands at a distance and three-dimensional orientation that is optimal for binding to the protein or other biological target. The invention can be practiced with structurally uncharacterized proteins, and is not limited by properties inherent in other NOE based and HSQC based methods. Moreover, the invention can be practiced to produce hybrid ligands from 3, 4, or even more individual ligands.

The invention can be most advantageously employed to improve the biological activity of ligands already known to exhibit a desired biological effect by covalently linking the known ligand to another active ligand discovered by the process of this invention. Covalently linking a newly discovered ligand to a ligand already known to be active has two primary advantages. First, the increased size of the hybrid ligand diminishes the likelihood that the first ligand could bind to receptors other than the intended biological target, and induce unwanted side effects. Second, the hybrid ligand draws upon the binding affinity of both ligands to bind the recognition domain of the biological target with higher affinity, and thereby enhances the biological activity of the individual ligands.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

FIG. 3 shows: (a) Section of proton-coupled HSQC spectrum of isotropic AMM in MBP with selected couplings annotated, and (b) Section of a proton-coupled HSQC spectrum of oriented AMM (α-methyl mannose) in MBP (mannose binding protein) with selected couplings annotated. The anomeric regions of the spectra are not shown. Anomeric splittings are 169.4 (±0.5) Hz for isotropic condition and 158.6 (±0.2) Hz for the oriented case.

FIG. 5 depicts AMM in fast exchange with the three equivalent CRDs of MBP. The 3-fold axial symmetry results in a direction of highest order along the rotor axis. Yellow spheres correspond to $Ca^{2+}$, black and red spheres to carbon and oxygen, respectively, of AMM. MBP is represented by a ribbon.

DISCUSSION

The present invention may be understood more readily by reference to the following detailed description of preferred embodiments of the invention and the Examples included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting.

Definitions and Use of Terms

As used in this specification and in the claims which follow, the singular forms "a," "an" and "the" include plural referents unless the context clearly dictates otherwise. Thus, for example, reference to "a ligand" includes mixtures of ligands, reference to "an NMR resonance" includes more than one resonance, and the like.

The "biological target" can be selected from any biological molecule that is activated or inhibited by ligand binding to a recognition domain on the compound. Biological targets encompassed by the invention thus include a diverse array of compounds including proteins, polypeptides, oligopeptides, and nucleic acids. Exemplary proteins include enzymes, transmembrane transporters, signal receptors and mediators, primary and secondary messengers, transcription and translation factors, and others. In a preferred method for practicing the invention, isotopically labeled molecules are used for the biological target, and substitute for the naturally occurring biological target.

"Ligands" useful in the invention can be any naturally occurring or synthetic compound, or fragment thereof, that binds to the recognition domain of a biological target. Recognition domains include both primary binding domains and regulatory domains. Ligands can thus be analogs of known substrates or inhibitors or regulators of biological activity. They can also be compounds with no previously identified biological effect. Inhibitor analogs, substrate analogs and regulator analogs can be covalently linked to one another or to any class of ligand to enhance activity by the process of this invention. Binding between ligand and biological target can be any form that causes the desired activation or inhibition, and includes ionic bonding, hydrogen bonding, and Van der Waals association. A particularly preferred class of ligands that are especially useful for illustrating the potential of the new methods are the mono-, oligo-, and polysaccharides.

The term "peptide" is used generically in this document to includes oligopeptides, polypeptides, and proteins, whether or not isotopically labeled.

The term "complex" refers to two or more distinct chemical compounds bound together by covalent bonds, electrostatic interactions (ionic bonds), hydrogen bonds, or Van der Waals association. The term includes ligands bound by proteins in which the ligands are in rapid exchange. Complexes are formed by mixing the biological target simultaneously or sequentially with the various ligands under circumstances that allow those ligands to bind the target. Means for determining those conditions are well known in the art.

General Discussion

As noted above, the present invention uses a novel paramagnetic-labeling technique to identify ligands that bind near one another on one or more recognition domains of a protein or a biological target, and to map the distances between ligands when bound to the biological target. Such information can advantageously be used to design hybrid ligands that contain a plurality of ligands covalently linked together substantially at the mapped distances.

Thus, in one aspect the invention provides a method for improving the binding affinity of a ligand for a biological target comprising: (1) preparing first NMR spectra of a first complex comprising the biological target and a paramagnetically labeled derivative of a first ligand; (2) preparing second NMR spectra of a second complex comprising the biological target and a second ligand; and (3) analyzing the spectra to determine whether the second ligand binds to the biological target within the paramagnetic zone of the paramagnetically labeled derivative; wherein steps (1) and (2) are performed simultaneously, consecutively, or in any order.

One embodiment (the indirect method) is characterized in that step (3) of the invention is performed by: (a) identifying peaks from the biological target on the first NMR spectra that are perturbed by the paramagnetic label; and (b) determining whether the second ligand perturbs peaks on the second NMR spectra that are also perturbed by the paramagnetic label. Another embodiment (the direct method) is characterized in that the first complex further comprises the second ligand, and step (3) is performed by determining whether the paramagnetically labeled derivative of the first ligand perturbs peaks associated with the second ligand.

In a further embodiment the invention provides deducing the distance of separation of the first and second ligands when bound to the biological target; and selecting or preparing a compound that contains the first and second ligands substantially at the distance. In a still further embodiment the invention provides deducing the relative three-dimensional orientations of the first and second ligands when bound to the biological target; and selecting or preparing a compound that contains the first and second ligands substantially in the relative orientations.

The invention is particularly useful for designing ligands for structurally uncharacterized proteins (uncharacterized because NMR resonances from the protein have not been sequentially assigned to the protein or because the three dimensional conformation of the protein is not known). Both pieces of information (assignment and three dimensional conformation) are typically critical to ligand design because the conformation of the protein dictates the complementary placement of ligand components. The three-dimensional conformation of the protein dictates the conformation of the ligand and, when the ligand must bridge different segments of the protein due to the protein's conformation, it also dictates the sequence of the ligand components to be linked and distances between them. The protein might be uncharacterized for any number of reasons: it may be too large, it may have low solubility, it may not be possible to produce or isolate the protein in adequate amounts with its natural three dimensional conformation, or it may not be possible to express the protein well enough for isotopic labeling (which is often used for NMR characterization of amino acid residues).

In one embodiment (the indirect method) the distances between binding sites for an uncharacterized protein are determined first by linking a paramagnetic label and a ligand known to bind to the protein in the protein's recognition domain. Paramagnetic labels can perturb (through loss of intensity or line broadening) the peaks on an NMR resonance spectra from nuclei that are within about 20 angstroms of the paramagnetic label. The level of perturbation is directly correlated to the distance between the paramagnetic label and the nucleus under observation, and the properties of the paramagnetic label. Thus, by forming a complex between the paramagnetically labeled ligand and a protein of interest, and constructing NMR spectra for the complex, one can identify peaks associated with protons within about 20 angstroms of the paramagnetical label, and calculate the distance from the paramagnetic label to the nuclei.

The next step is to form a complex between a second ligand and the protein under observation, and to construct another set of NMR spectra for the complex. If the second ligand binds to the protein, then it will perturb peaks associated with atoms on the protein to which the ligand is bound (usually by alteration of chemical shift). If the second ligand perturbs one or more of the same peaks perturbed by the paramagnetic label, then one knows that the ligand has bound to the protein within the paramagnetic zone of the paramagnetic label, which can be within about 20 angstroms of where the first ligand binds the protein. Because one can determine the distance between the paramagnetic label and the nuclei whose peaks are perturbed, one is also able to determine the distance between the first and second ligands when bound to the protein. Using appropriate chemical synthetic techniques, one can then construct a new hybrid ligand from the first and second ligands in which the first and second ligands are bound at a distance approximating their distance when bound to the protein.

Thus, in one embodiment (the indirect method) the invention provides a method for improving the binding affinity of ligands for biological targets comprising: (1) preparing first NMR spectra for a first complex comprising the biological target and a paramagnetically labeled derivative of a first ligand; (2) identifying peaks on the first NMR spectra that are perturbed by the paramagnetic label; (3) preparing second NMR spectra for a second complex comprising the biological target and the second ligand, and (4) determining whether the second ligand perturbs peaks on the second NMR spectra that are also perturbed by the paramagnetic label.

These steps can be performed sequentially, simultaneously, or in any order. For example, spectra from the second complex could be analyzed first to determine which resonances from the biological target are perturbed by the second ligand, followed by NMR spectral analysis of the first complex to determine whether the paramagnetic label perturbs the same resonances. Spectral data can also be deduced for a complex comprising the biological target and both the first and second ligands, to ensure that the ligands do not interfere with one another's binding. Such analysis can be performed as an added step to the above method or, although it makes interpretation of the data more complicated, the first ligand can be added to the second complex before analysis, or the second ligand can be added to the first complex before analysis.

In another embodiment (the direct method) ligands are screened by forming a tertiary complex of the biological target, the paramagnetically labeled first ligand, and the second ligand, preparing NMR spectra for the complex, and determining whether the paramagnetic label perturbs peaks associated with the second ligand. One typically determines whether the paramagnetic label perturbs any peaks associated with the second ligand by comparing the tertiary complex spectra to NMR spectra of a binary complex of the biological target and second ligand without the paramagnetic label. One typically excludes perturbation by direct interaction of the first and second ligand by examining a spectrum of ligands one and two in the absence of the target protein. If the paramagnetic label perturbs one or more of the peaks associated with the second ligand only in the presence of protein, then one knows that the ligand has bound to the protein within the paramagnetic zone of the paramagnetic label, which can be within about 20 angstroms of where the first ligand binds the protein. Because one can estimate the distance between the paramagnetic label and the nuclei whose peaks are perturbed by the level of perturbation (or degree of relaxation) one is also able to determine the distance between the first and second ligands when bound to the protein. Using appropriate chemical synthetic techniques, one can then construct a new hybrid ligand from the first and second ligands in which the first and second ligands are bound at a distance approximating their distance when bound to the protein.

Thus, in another embodiment (the direct method) the invention provides a method for improving the binding affinity of ligands for biological targets comprising: (1) preparing first NMR spectra of a first complex comprising a biological target, a paramagnetically labeled derivative of a first ligand, and a second ligand; (2) preparing second NMR spectra of a second complex comprising the biological target and the second ligand; (3) preparing third NMR spectra of a mixture of the paramagnetically labeled derivative of a first ligand and the second ligand in the absence of the biological target; and (4) analyzing the spectra to determine whether the paramagnetically labeled derivative of the first ligand perturbs peaks associated with the second ligand when bound to the biological target; wherein steps (1), (2) and (3) can be performed consecutively in any order. In a further embodiment, the invention further comprises deducing from the NMR spectral data the distance between the first and second ligands when bound to the biological target; and selecting or preparing a hybrid ligand that contains the first and second ligands covalently linked substantially at the bond distance.

The method of this invention can be performed by screening more than one ligand at a time, i.e. by mixing a plurality of second ligands with the target, preparing NMR spectra for the mixture, and determining whether any of the second ligands bind the target within the paramagnetic zone of the paramagnetically labeled first ligand. Where the process screens a mixture of ligands, and where one observes that the mixture of ligands perturbs peaks that are also perturbed by the paramagnetic label (in the indirect method), or that the paramagnetic label perturbs peaks from the ligands (in the direct method), additional steps are performed to identify which specific ligand(s) contained in the mixture is binding to the biological target. Those additional steps comprise the steps of exposing the biological target individually to each ligand of the mixture, generating NMR spectra of the biological target that has been individually exposed to each compound; and determining from each individual spectrum which ligand(s) perturb peaks that are also perturbed by the paramagnetic label, or which ligand generates peaks that are perturbed by the paramagnetic label.

The method of this invention can be practiced using any spectroscopic method that analyzes and presents NMR data, including one and two dimensional NMR spectroscopy. The indirect method is most preferably practiced using two-dimensional $^{15}N/^{1}H$ heteronuclear single quantum correlation (HSQC) spectra. Isotopic labels other than $N^{15}$ can be used to practice the invention including, without limitation, $^{2}H$ labeled molecules, $^{13}C$ labeled molecules, $^{15}N$ labeled molecules, and $^{31}P$ labeled molecules. Particular signals in a two-dimensional $^{15}N/^{1}H$ correlation spectrum correspond to specific nitrogen and proton atoms in the biological target (e.g., particular amides of the amino acid residues in the protein). Perturbations of resonances will be marked by shifts in peaks. To facilitate processing of the NMR data, computer programs are used to transfer and automatically process the multiple two-dimensional NMR data sets. Because the $^{15}N/^{1}H$ signals corresponding to the backbone amides of the proteins are usually well-resolved, the chemical shift changes for the individual amides can be readily monitored using this technique.

Isotopic labeling is not necessary to practice this invention. However, isotopically labeled molecules are often preferred because of the excellent dispersion of signals typically emitted by isotopes from the molecule. For example, the excellent dispersion of the signals from the amide $^{1}H$—$^{15}N$ of $^{15}N$ labeled proteins, combined with the high degree of sensitivity of the HSQC experiment, typically allows the effect of the paramagnetically labeled ligand on each amide residue within about 20 Å of the ligand binding site in a $^{15}N$-labeled protein to be readily evaluated.

Means for generating two-dimensional $^{15}N/^{1}H$ correlation spectra are well known in the art, as discussed more particularly in D. A. Egan. et al., Biochemistry, 32:8, pgs. 1920–1927 (1993), and Bax. A., Grzesiek, S., Acc. Chem. Res., 26:4, pgs. 131–138 (1993), the disclosures from which being hereby incorporated by reference. Detailed descriptions of means of generating such two-dimensional $^{15}N/^{1}H$ correlation spectra are set forth hereinafter in the Examples.

The direct method is preferably practiced using one dimensional $^{1}H$ spectra. Resolution of peaks in these spectra from small ligands is usually adequate. No isotopic labeling of biological target or ligand is required. Means of generating such spectra are well known in the art.

Peptides used as biological targets in this invention can be isolated from naturally occurring sources for use, or produced recombinantly. Means for preparing recombinant expression vectors that contain polynucleotides encoding specific polypeptides are well known in the art. In a similar manner, means for transforming host cells with those vectors and means for culturing those transformed cells so that the polypeptide is expressed are also well known in the art. The peptide target is preferably produced in recombinant form from a host cell transformed with an expression vector that contains a polynucleotide that encodes the peptide. Isotopically labeled peptides are produced by culturing the transformed host cell in a medium that contains an assimilable source of $^{15}N$ such that the recombinantly produced peptide is labeled with $^{15}N$. Assimilable sources of $^{15}N$ are well known in the art. A preferred such source is $^{15}NH_4Cl$.

$^{2}H$ substituted proteins can also be used for optimum performance. Such proteins can be produced in E. coli by growing on $^{2}H_2O$; higher levels of $^{2}H$ can be attained using a deuterated carbon source as well. Deuterons on $^{15}N$ labeled amide sites will then be back-exchanged for protons from $^{1}H_2O$. The resulting low density of protons minimizes $^{1}H$—$^{1}H$ relaxation and limits relaxation contributions to those from 15N-1H pairs.

As shown above, paramagnetic labeling can provide valuable information about distances between the protons (or other nuclei) on a molecule that gives rise to NMR signals. By linking the paramagnetic label to a known ligand for a biological target, and constructing NMR spectra for other potential ligands in the presence of the paramagnetically labeled molecule and target, one can identify protons on the other potential ligands or biological target whose NMR signal is perturbed by the paramagnetic label. Paramagnetic labels can perturb NMR peaks of protons located more than 20 Å away from the paramagnetic label, although the zone of such perturbations ultimately depends on the paramagnetic label used and its electronic magnetic moment. Paramagnetic labeling is thus an optimal technique for studying the recognition domains of proteins because the distance between binding sites on the recognition domains of proteins often is within the paramagnetic label's zone of influence. Moreover, the paramagnetic labeling techniques can identify binding sites on discontinuous strands of the protein, to design ligands that bridge across space to discontinuous strands, because the paramagnetic label's influence is limited predominantly by distance alone.

Paramagnetic labels with which the invention can be practiced generally include any type of molecule that relaxes the NMR signals of neighboring nuclei, provided the molecule can be suitably linked to a ligand under study, and will not substantially interfere with the binding of the ligand to a biological target. Paramagnetic relaxation probes contain one or more unpaired electrons that provides an efficient mechanism for the relaxation of neighboring nuclei via dipolar coupling. Preferred paramagnetic labels include nitroxide paramagnetic labels such as TEMPO 2,2,6,6-tetramethylpiperidine-1-oxy-4-yl, and metal chelates.

Due to the magnitude of the electron magnetic moment associated with nitroxide moieties, nitroxide paramagnetic labels typically interact with neighboring nuclei over a radius of about 20 Å. In contrast, proton-proton NOEs are limited to separations of less than 5 Å. Thus, paramagnetically labeled ligands can be utilized to obtain long-range distance information about complexes formed between the ligand and the biological target.

Paramagnetic labels can be attached to ligands using any available covalent linking technique. In the case of oligosaccharides, bonding can occur through an amino group on the oligosaccharide. The amino group can be naturally occurring, or it can be synthetically introduced at the reducing end of the oligosaccharide. Condensation with a carboxyl group on the paramagnetic label or chelate produces the desired paramagnetically labeled ligand.

As mentioned above, the NMR spectra of paramagnetically labeled molecules are preferably used to determine the distance between the paramagnetic label and the protons whose peaks are perturbed by the paramagnetic label. There are two principal ways to estimate distances from intensity based measurements. One is to use estimates of protein reorientational correlation times and relaxation times measurements ($T_1$, $T_2$) to calculate a distance. The other uses a, calibration distance taken from known distances in the ligand or in homologous sites of other proteins. Methods for modeling the perturbations, and using the models to calculate the distances, are published in a number of references, including Johnson et al., J. Mol. Biol. (1999) 287; 609–625.

Example 2 shows how the distances were calculated using a paramagnetically labeled analog of the carbohydrate N-acetyl Lactosamine (LacNac), bound to Galectin-3, and a calibration distance taken from the known protein structure. The lack of distance restraints with $r_{eff}$ less than 11 Å, caused by the efficiency of paramagnetic relaxation of the paramagnetic label, could be addressed by studying Galectin-3 titrated with smaller quantities of TEMPO-labeled LacNac or with mixtures of the TEMPO-labeled LacNac in its reduced and oxidized forms in order to identify the amides closest to the bound nitroxide.

The binding affinity of the hybrid ligands for the protein can be further enhanced by covalently linking the first and second ligands in a geometry that achieves optimum orientation for binding to the protein. The relative three dimensional orientations of the ligands when bound to the biological target can be determined using X-ray crystallography when the protein cystalizes and a structure can be determined, or by NMR-based techniques when crystals are not available. One suitable NMR-based approach relies upon nuclear Overhauser effects (NOEs) between ligands and protein when a plurality of ligands are bound to the protein. The use of NOE studies to design ligands based upon three dimensional data is described in detail in U.S. Pat. No. 5,989,827 to Fesik, the disclosure of which being hereby incorporated by reference. The method uses NOE data to model the geometry of ligands in relation to the surface of the protein. If the three-dimensional structure and amino acid sequence of the biological target is known, then one is able to determine the geometry of the ligands relative to one another.

A preferred NMR-based technique for evaluating the relative orientations of ligands, discussed in more detail below, depends upon the observation and interpretation of dipolar coupling within the individual ligands when the ligands are bound to a target. By generating a field ordered state of the first and second ligands when bound to the protein, one can acquire NMR spectra from which dipolar couplings within the ligands can be analyzed, and from which the spatial orientation of dipole-dipole interactions can be deduced. This usually requires an independent determination of a ligand binding constant from NMR or other data. With knowledge of the spatial orientation of the dipole-dipole interactions, one is then able to model the spatial orientation of the ligands when bound to the protein, and covalently link the ligands at such orientation.

Most importantly, the method is not limited by limitations inherent to NOEs. For example, NOEs might not give sufficient information to deduce the relative three dimensional orientations of the ligands when bound to the protein because:

(1) The protein is not sufficiently characterized, in the sense that protein NMR resonances are not assigned to specific amino acids in the sequence of the protein;

(2) The three dimensional configuration of the protein is not known;

(3) NMR observable protons on the first and second ligands are not sufficiently close to NMR observable protons on the surface of the protein to characterize the relative three-dimensional orientation of the ligands by NOEs. For sufficient magnetization transfer to occur, protons typically must be less than 5 Å apart. This occurs for example when the first and/or second ligand is a molecule such as a mono-, oligo-, or polysaccharide which gives few protein-ligand NOEs. Characterization by traditional NMR methods of oligosaccharide-protein interactions is difficult because the hydrogen-bonding networks involving hydroxyl protons on the sugars are often part of the interface between protein and oligosaccharide. The hydroxyl protons are then the ones in closest proximity to protein protons, but they exchange rapidly with protons in bulk water making their NMR resonances hard to observe. In these difficult cases, residual dipolar data can offer a valuable alternative, where the data can in principle constrain both bound ligand geometry and ligand orientation relative to the protein binding site;

Thus, in another embodiment the invention provides a method of increasing the binding affinity of two or more ligands for a protein comprising:
  a) deducing from NMR spectra the distance between first and second ligands when bound to a protein,
  b) deducing from NMR spectra the relative three-dimensional orientations of the first and second ligands when bound to the protein, and
  c) selecting or preparing a compound that contains the first and second ligands substantially in the relative three-dimensional orientations determined in step (b) substantially at the distance determined in step (a),
  d) wherein:
    i) NMR resonances assigned to a sequence of the protein are not used for step (a),
    ii) the three dimensional configuration of the protein is not used for step (b),
    iii) the first and/or second ligand is a mono-, oligo-, or polysaccharide, or
    iv) NMR observable protons on the first and second ligands are not sufficiently close to the surface of the protein to characterize the relative three-dimensional orientation of the ligands by NOEs.

The method preferably uses the paramagnetic labeling process discussed herein to determine distances between ligands. The method also preferably uses dipolar coupling information derived from a field ordered state of the ligand/protein complex to derive three dimensional orientations of the ligands when bound to the target.

Residual dipolar coupling relies upon the fact that when molecules are partially ordered in a magnetic field, vectors connecting magnetic nuclei in the molecules depart from a complete isotropic sampling of all directions in space as they tumble in solution. This gives rise to a contribution to splitting of NMR resonances that depends on the magnetic properties of the interacting nuclei, the internuclear separation (r) and the angle ($\theta$) that the vector makes with the magnetic field. When the nuclei are directly bonded as in $^1H$—$^{15}N$ or $_1H$—$^{13}C$ pairs, the $1/r^3$ distance-dependence of the interaction can be regarded as being determined by the bond length and the primary variable becomes the orientation of the bond relative to the magnetic field as characterized by the angle $\theta$. The functional dependence of the dipolar couplings is ($\frac{1}{2}(3 \cos^2 \theta - 1)$), where the parentheses denote an average over an orientation distribution, and the resulting interaction appears as an addition to the normal one bond scalar couplings. Several means of producing field-ordered states are available, including inherent orientation due to the large anisotropies in the magnetic susceptibilities of some molecules, orientation due to the interaction of molecules with lipid bicelles that form field-oriented liquid crystals, and interaction with filamentous bacteriophage that also form field-oriented liquid crystals.

The interpretation of residual dipolar data preferably takes one of two routes: incorporation of individual bond constraints as penalty functions in simulated annealing protocols for molecular structure determination, and extraction of order tensors that directly describe the direction and level of ordering from the point of view of a coordinate frame fixed in a rigid molecular ligand. The latter approach is preferred. An order tensor is a 3×3 matrix with elements ($\frac{1}{2}(3 \cos \theta_i \cos \theta_j - \delta_{ij})$) written in terms of direction cosines that relate Cartesian axes of an arbitrarily chosen molecular axis system to the magnetic field direction. Because the matrix is traceless and symmetric, there are only five independent elements. An order matrix in an arbitrarily chosen frame of a molecular ligand is difficult to interpret, but if diagonalized the five independent variables turn into a principal order parameter, an asymmetry parameter and three Euler angles relating the diagonal, or principal frame, to the original molecular frame. If ligands of interest experience a common source of order, as they would if they were parts of a rigid ligand-protein complex, the directions and levels of the orientation should appear the same from the point of view of each ligand when a model for the ligands is assembled with proper ligand orientations.

The key to using this procedure is having an approximately rigid ligand, or pieces within a ligand, with enough potential dipolar coupled pairs to determine the five elements of an order tensor. For a $^{15}$N-labeled protein, pairs of $^1$H—$^{15}$N spins are clearly abundant and much of the protein backbone can be considered rigid. In oligosaccharides, individual pyranose rings frequently prefer a $^4C_1$ configuration which can be considered to have approximately rigid geometry and $^1$H—$^{13}$C pairs are abundant. There are a number of ways of accurately determining the splittings of resonances from these pairs but the easiest is simply to collect $^1$H—$^{13}$C heteronuclear single quantum coherence (HSQC) spectra, without decoupling in one of the frequency domains.

As mentioned above, the present invention is especially useful when screening for ligands that can be combined with a ligand known to exhibit some relevant biological activity. Individual ligands for screening can be selected inter alia on the basis of size and molecular diversity. Compounds in the collection can have different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings) for maximizing the possibility of discovering compounds that interact with widely diverse binding sites on biological targets. To discover molecules that bind more tightly to the protein, molecules are selected for testing based on the structure/activity relationships from the initial screen and/or structural information on the initial leads when bound to the protein. By way of example, the initial screening may result in the identification of ligands, all of which contain an aromatic ring. The second round of screening would then use other aromatic molecules as the test compounds.

Knowledge of the spatial orientations of the ligands, combined with knowledge of the distance separating them when bound to the biological target, is then used to select linkers to link two or more ligands together into a single "hybrid ligand" that contains all of the ligands. The design of the linkers is based on the distances and angular orientation needed to maintain each of the ligand portions of the single entity in proper orientation to the target.

The three-dimensional conformation of suitable linkers is well known or readily ascertainable by one of ordinary skill in the art. While it is theoretically possible to link two or more ligands together over any range of distance and three-dimensional projection, in practice certain limitations of distance and projection are preferred. In a preferred embodiment, ligands are separated by a distance of less than about 20 or 15 angstroms.

Ligands are linked to one another using those portions of the ligand not directly involved in binding to the biological target. Depending upon the ligands, the molecules may also be combined or joined (linked) directly to each other without intervening linker units. The high affinity ligand produced from the combined ligands preferably shows an increase in binding potency to the biological target in relation to any one of the individual ligands. The present invention, therefore, includes high-affinity ligands designed by the processes shown herein wherein said high-affinity ligand has an increase in binding potency to the given biological target over the at least two ligands which bind to distinct sites on the given biological target.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Direct Interactions of Paramagnetic Labeled LacNAc and UDP Bound to β-1→4-Galactosyltransferase As an illustration of NMR assisted identification of potential drug ligands using a moderately large protein that is not isotopically labeled we have performed preliminary studies using β-1→4-galactosyltransferase (~30 kDa domain). These experiments use a nitroxide paramagnetic labeled substrate analogue to induce relaxation of resonances from nearby protons on a bound second ligand. Enhanced relaxation is reflected in increased line widths, with the increases being inversely proportional to the sixth power of the paramagnetic label to proton distances.

The substrate chosen for construction of a paramagnetic labeled analog is N-acetyllactosamine (LacNAc, Structure 1). The second ligand was not found with a general screening procedure, but was chosen to be uridine diphosphate (UDP, Structure 2), a product released from the normal glycosyl donor, and known to bind in the protein active site. The paramagnetic labeled analog, LacNAc-TEMPO (O-β-D-galactopyranosyl-(1→4)-3-acetamido-1,2-dideoxy-1-(N-2,2,6,6-tetramethylpiperidino-1-oxyl-4-carboxamido)-β-D-glucopyranoside) was synthesized by condensing 4-carboxy-TEMPO (4-carboxy-2,2,6,6-tetramethylpiperidinyloxy) with 1-amino-LacNAc. The enzyme and UDP concentrations were kept constant at 0.1 mM and 1 mM respectively while the concentration of LacNAc-TEMPO was varied from 0 to 16 mM. We chose to monitor the peak from H6 of UDP to demonstrate an ability to observe line broadening of a resonance from a proton known to be within 15 Å of the paramagnetic label. This peak is shown in the top spectrum of FIG. 1 in the absence of paramagnetic label. The bottom spectrum shows the peak in the presence of 16 mM LacNAc-TEMPO. Approximately 50% broadening is observed. The marked peaks are low level contamination from synthesis of the paramagnetic label. Control experiments were run to insure that the broadening was not a result of non-specific interactions between the paramagnetic labeled LacNAc and UDP.

Structure 1. (Top) LacNAc-TEMPO
Structure 2. (Bottom) UDP

Example 2

Distance Mapping of HSQC Cross-peaks for Galectin-3

Binding of a nitroxide paramagnetic labeled analog of the carbohydrate, N-acetyl Lactosamine (LacNAC), to Galectin-3, a mammalian lectin of 14 Kda size, has been studied to map out the binding sites of carbohydrate on the protein surface. The 14 kDa carbohydrate recognition domain of galectin-3 can be expressed in *E. coli* as an $^{15}$N labeled product by modification of the procedures set forth in Seethraman J, Kanigsberg A, Elaaby R, Leffler H, Barondes S H, Rini J M, *J. Biol. Chem* 273: 13047–13052 (1998).

Alternatives to the nitroxide labeled N-acetyllactose amine could be used; for example an EDTA chelate analog loaded with a paramagnetication $Gd^{3+}$. N-acetyllactosamine oligomers are commonly prepared by a strategy that employs an oxazoline at the reducing end of an intermediate oligomer to add additional lactosamine units through a free hydroxyl. A hydroxylated and protected EDTA analog can be used instead of a second N-acetyllactosamine unit to produce the chelate.

Figure 1:
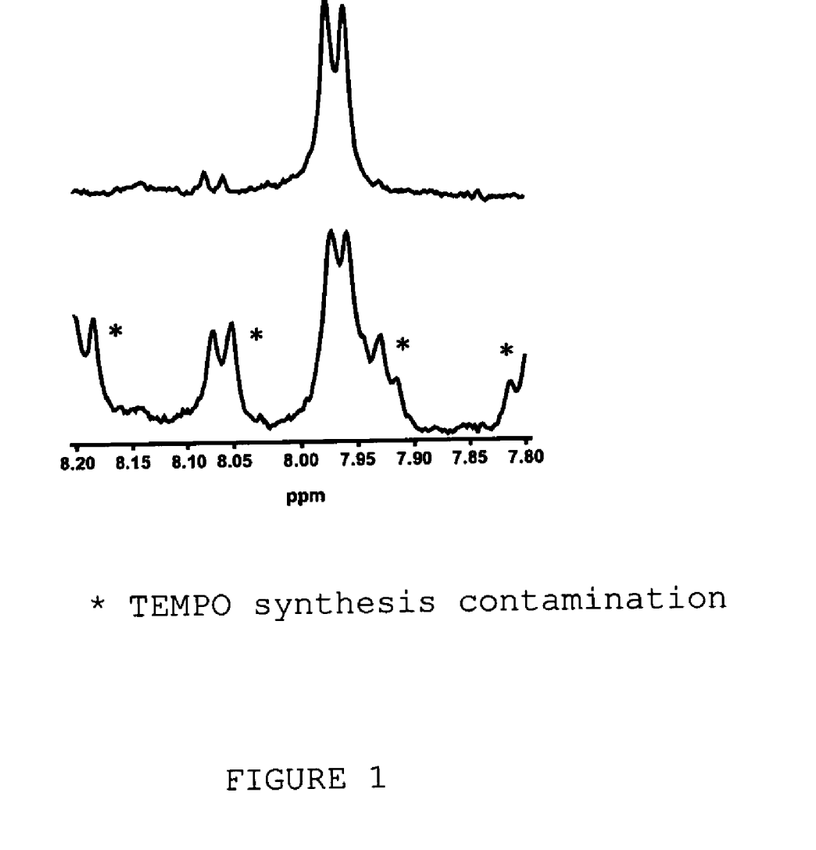
FIG. 1 illustrates the line broadening in a one dimensional NMR spectrum of a resonance from a proton known to be within 15 Å of a paramagnetic label covalently attached to a second compound when both are bound to a protein target. The top spectrum displays the isolated resonance of H6 of uridine 5-diphosphate (UDP) when the UDP is in the presence of the protein, but not the paramagnetically labeled compound. The bottom spectrum displays the isolated resonance of H6 of UDP when the compound with a paramagnetic label is bound to the protein, and the label is within 15 Å of H6 protein bound UDP.
Figure 2A:
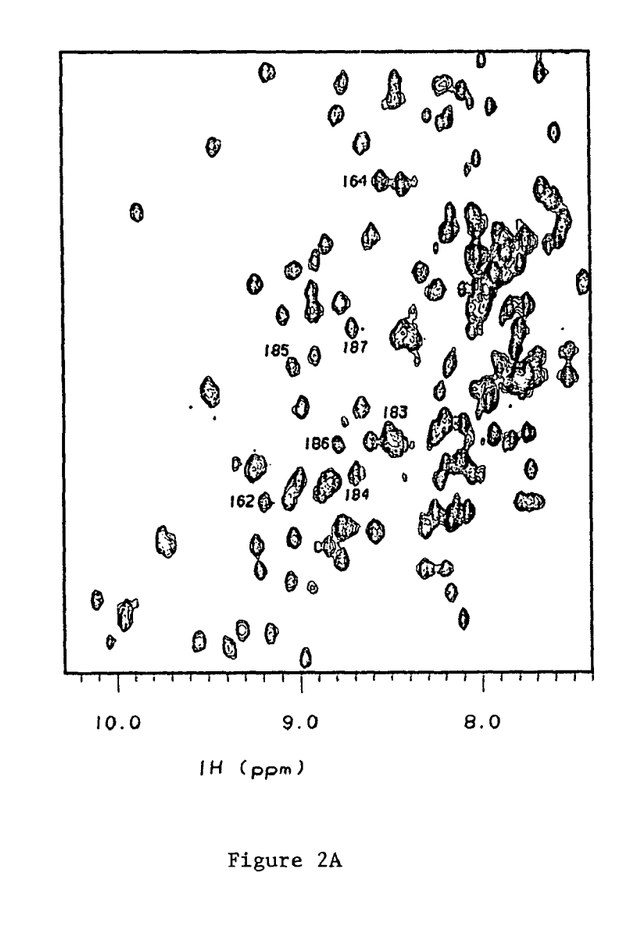
FIG. 2 shows two-dimensional NMR $^{15}$N HSQC spectra of Galectin-3, and Galectin-3 bound by paramagnetically labeled LacNAc (2a, 2b respectively), and how perturbations of intensities of cross-peaks in the $^{15}$N HSQC spectrum can be used to identify protein residues within 15 Å of the binding site of the LacNAc paramagnetic label.
Figure 2B:
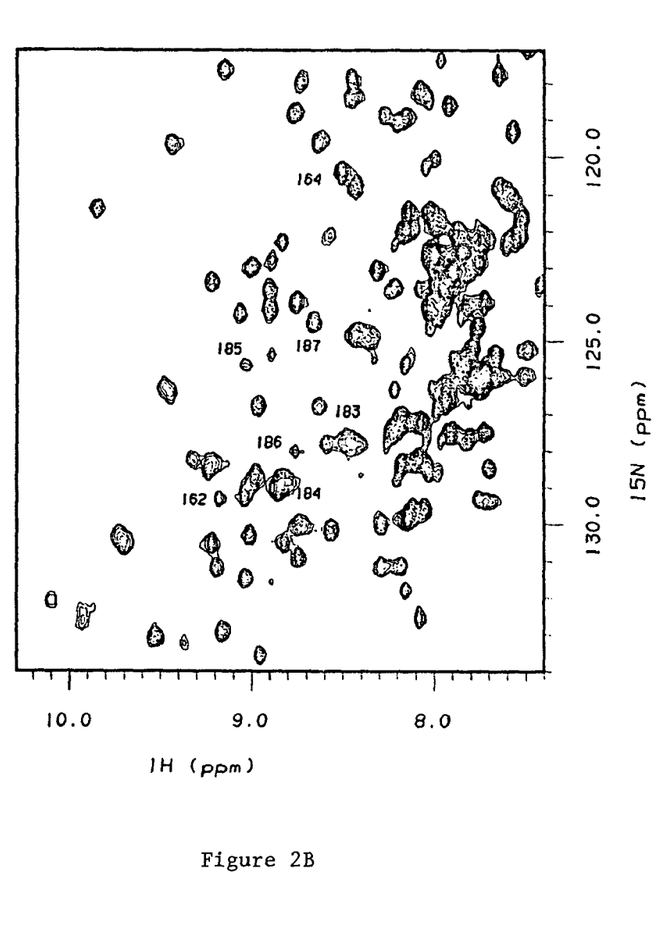

Perturbations of intensities of cross-peaks in the $^{15}$N HSQC spectrum of intact Galectin-3 due to the bound paramagnetic label has identified the protein residues potentially proximate to the binding site for LacNAC (FIGS. 2a, 2b). The cross-peak from residue 184 has been reduced most and is just below detection in FIG. 1b. Normally all cross-peaks will not have been assigned and we wish only to label peaks according to distance from the paramagnetic label.

There are two ways to estimate distances from intensity based measurements. One is to use estimates of protein reorientational correlation times and relaxation time measurements ($T_1$, $T_2$) to calculate a distance. The other, the one illustrated here, uses a calibration distance taken from closest approach distances in homoogous sites of known proteins. A relation of the type $\Delta I_1/\Delta I_2 = r_2^6/r_1^6$ (where $\Delta I_1$ and $\Delta I_2$ are the intensity changes and $r_1$ and $r_2$ are corresponding distances from the bound paramagnetically label) obviates the need for knowledge of the correlation time $\tau_c$ of the molecule. Here we use the distance to the amide of residue 184 as a calibration distance. Based on the geometry of the ligand and the known structure of this protein, the calibration distance can be estimated to be 11–12 Å for the most severely broadened peak still visible after complete binding of ligand with the protein. Distances will be similar for the most broadened peaks of unknown proteins, for which the spin label extends from the last ligand moiety believed to occupy the building site. Distances obtained by this second method are compared with actual distances calculated from the X-ray crystal structure of Galectin-3 in Table 1.

TABLE 1

| Residue | X-Ray (Å) | Paramagnetic label (Å) |
| --- | --- | --- |
| 182 | 14.04 | 14.58 |
| 183 | — | — |
| 184 | 11.90 | 11.90 |
| 185 | 14.20 | 15.60 |
| 186 | 14.88 | 15.89 |
| 187 | 17.20 | 17.67 |
| 162 | 18.90 | 18.40 |
| 164 | 19.13 | 20.80 |

Example 3

Residual Dipolar Coupling Derived Orientational Constraints on Ligand Geometry in a 53 kDa Protein-Ligand Complex The following procedure exemplifies the use of residual dipolar coupling information to model the three dimensional conifguration of α-methyl mannoside (AMM) in association with the carbohydrate recognition domain (CRD) of mannose-binding protein. (MBP) The reader is presumed to be familiar with the background of such a technique, and the various assumptions that underly the technique. For a more detailed discussion of the procedure, the reader is referred to P. J. Bolon, H. M. Al-Hashimi and J. H. Prestegard (1999) Residual Dipolar Coupling Derived Orientational Constraints on Ligand Geometry in a 53 kDa Protein-Ligand Complex, *J. Mol. Biol.* 293, 1070115. The method can be readily adapted to determine the relative three dimensional orientations of two or more ligands when complexed with a receptor protein.

Preparation of MBP-A

MBP-A is an expression product from the pIN-IIIom-pA-2 plasmid (1), and was expressed as described (2). Briefly, competent JA221 cells were transformed with DNA plasmid and colonies selected from LB-amp plates for use in a starter culture in an LB-amp medium. Starter culture was grown to saturation overnight at 37° C. and used to inoculate five liters of LB-amp medium, which grew to $A_{550}$ of 0.8. MBP-A production was then induced with IPTG and additional growth allowed for 2.5 hours. Cells were harvested by centrifugation at 4000 g, the pellet was resuspended in 10 mM Tris-Cl (pH 7.0) and then lysed by sonication. The insoluble pellet from 18,000 g centrifugation was solubulized in 6 M guanidinium chloride, 0.1 M Tris-Cl (pH 7.0), and clarified by centrifuging at 138,000 g for 30 minutes at 4° C. Dialysis of the centrifuge extract with 25 mM Tris-Cl, 1.25 M NaCl, 25 mM $CaCl_2$ over 48 hours and centrifuging at 138,000 g provided the dialysate which was purified by affinity chromatography on a mannose-Sepharose column. Elution with 25 mM Tris-Cl, 1.25 M NaCl and 2.5 mM Na2EDTA followed by reconstitution by dialysis against 10 mM NaCl, 1 mM Tris-Cl, 25 mM $CaCl_2$ afforded 10 mg of MBP-A from a five liter growth culture.

Preparation of AMM

AMM was synthesized from [$^{13}C_6$] glucose by minor modification of a described method (3). Briefly uniformly $^{13}C$-labeled D-glucose was protected as the penta-acetate with acetic anhydride, and the crude material brominated with HBr/AcOH. Reduction with Zn/aqueous AcOH provided the desired tri-O-acetyl-D glucal, which was used in a Ferrier reaction with methanol/Dowex H+ to give (α-methyl-2,3-dideoxy-4,6-di-O-acetyl-D-glucopyranoside. Purification by silica gel chromatography; followed by treatment of the anhydrous material with $OsO_4$ in pyridine afforded the desired diacetylated α-methyl mannoside. Flash chromatography followed by deacetylation with NaOMe/MeOH provided AMM in an 20% over yield. Use of this $^{13}C$-enriched product enhances the sensitivity of NMR experiments, but a natural abundance product can be substituted if loss of sensitivity is compensated with longer spectral acquisition times.

Figure 3A:
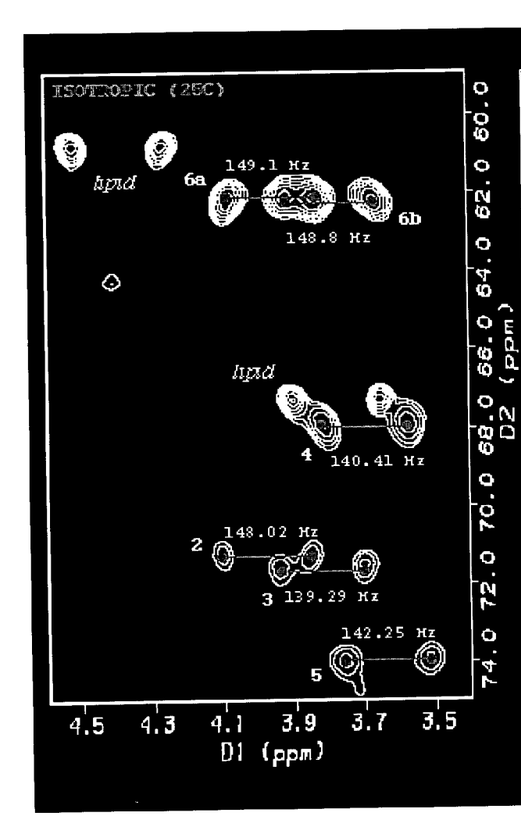
Figure 3B:
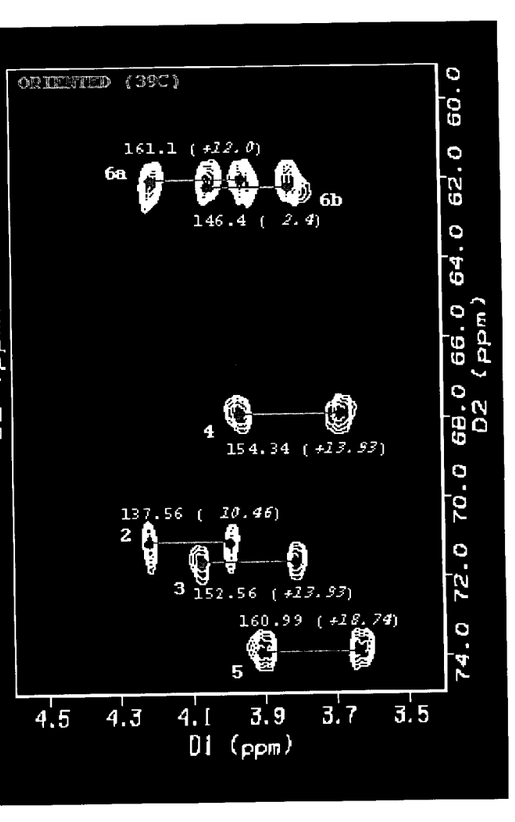

Measurement of Residual Dipolar Couplings in AMM Complexed to MBP $_1H$—$^{13}C$ HSQC NMR spectra of $^{13}C$-enriched AMM in the presence of an equimolar amount of MBP dissolved in a dilute bicelle medium are shown in FIGS. 3(a) and (b) at temperatures of 25° C. and 39° C., respectively. The data were acquired in the absence of $^{13}C$ decoupling during acquisition, and the one bond $^{13}C$—$^1H$ couplings are shown as frequency domain splittings in the proton dimension. The magnitudes of these couplings and the corresponding errors extracted using a Bayesian parameter estimation method are shown on the spectra. Residual dipolar contributions for individual C—H bond vectors calculated from the differences in couplings measured at 25° C. (isotropic) and 39° C. (aligned) are shown in Table 2 ($D_{obs}$).

in Table 2 ($D_{free}$). Again, couplings and associated errors were extracted using a Bayesian parameter estimation method.

Interpretation of residual dipolar contributions of a ligand in a protein-bound state will, in general, require separation of the contribution from the free state using known binding properties. The observed residual dipolar couplings measured in the AMM/MBP complex (Table 2, $D_{obs}$) will be a population weighted average from the free ($N_{free}$) and bound ($N_{bound}$) states, such that:

$$D_{obs}=N_{free}D_{free}+N_{bound}D_{bound} \quad (1)$$

The fraction of AMM free and bound ($N_{free}$ and $N_{bound}$) can be calculated from the dissociation constant and known protein-ligand concentrations. Using a previously determined binding constant (approx. 1 mM) approximately 40% of AMM is in fact bound to MBP leaving approximately 60% of AMM free in solution. Residual dipolar couplings originating from the bound state ($D_{bound}$) calculated from equation (1) are shown in Table 2.

Order Tensor Calculation in AMM

Figure 4:
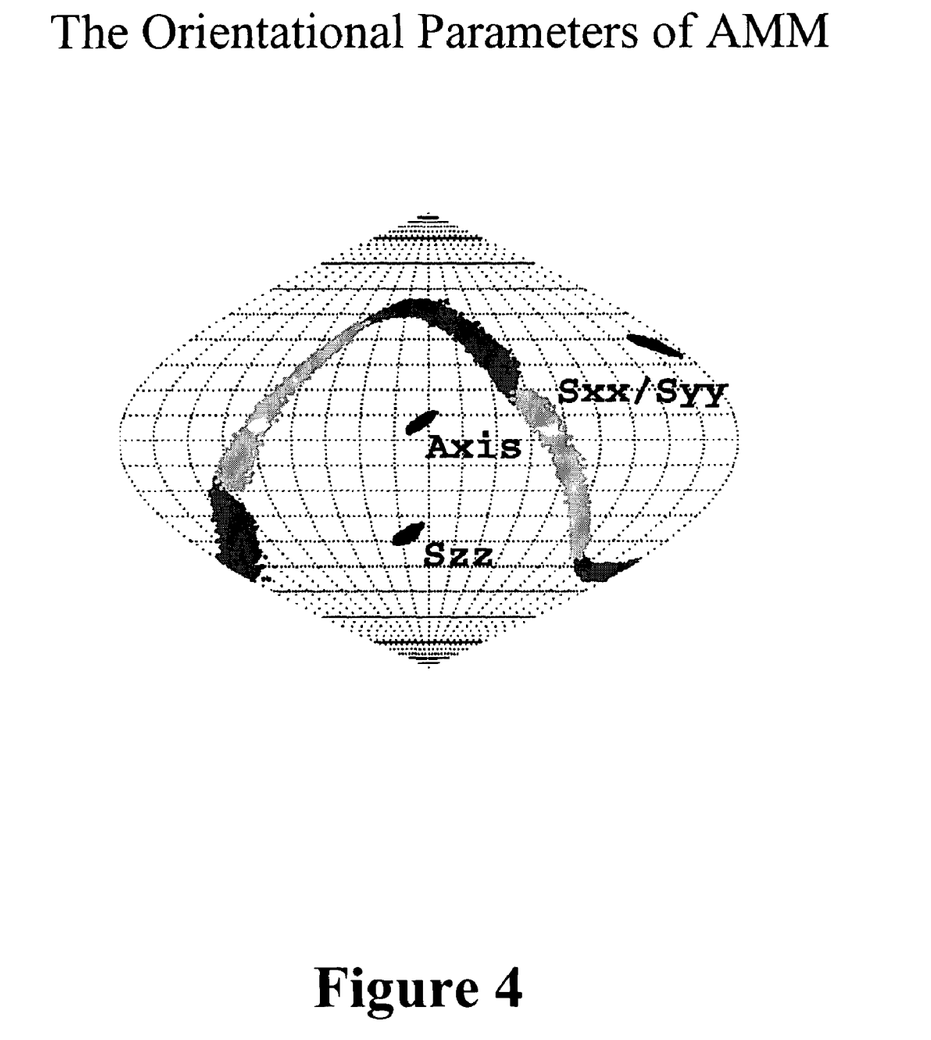
FIG. 4 shows a Sauson-Flaumsteed projection of the directions of highest order for oriented AMM in the presence of MBP, with a clear depiction of axial symmetry. The molecular cordinate frame for AMM was defined by placing the y-axis along the C1-H1 vector and the z-axis normal to the plane defined by H1-C1-OMe.

Using AMBER-minimized structure coordinates for AMM (8) and five residual dipolar couplings measured in the sugar ring in simple bicelle solution, the five elements of the order matrix were determined using a singular value decomposition approach (6). The initial molecular coordinate frame for AMM was defined by placing they-axis along the C1-H1 vector and the z-axis normal to the plane defined by H1-C1-OMe. The five elements of the order tensor for AMM determined from couplings for the MBP-bound state ($D_{bound}$) were determined using a singular value decomposition method, and the directions of the principal axes are depicted in FIG. 4(b) using a Sauson-Flaumsteed projection (10).

NMR Spectroscopy

NMR spectroscopy was performed as follows: Two samples were prepared: (1) a 1 mM MBP-A, 1 mM AMM, 10 mM NaCl, 1 mM Tris-Cl, 25 mM CaCl, (pH 7) in 500 µL of 5% (w/v) bicelle (DMPC/DHPC 3:1 molar ratio) solution in $^2H_2O$; and (2) a 2 mM AMM, 10 mM NaCl, 1 mM Tris-Cl, 25 mM $CaCl_2$ (pH 7) solution in 5% (w/v) bicelle (DMPC/DHPC 3:1) control sample. These were prepared as described (4) using one bicelle stock solution. All NMR experiments described below were conducted on an Inova 600 MHz NMR spectrometer equipped with z-axis pulsed-

TABLE 2

| Residual dipolar couplings for bound and free AMM | | | | |
|---|---|---|---|---|
| Data Set | $C_1$—$H_1$(Hz) | | | |
| $H_4$(Hz) | $C_5$—$H_5$(Hz) | $C_2$—$H_2$(Hz) | $C_3$—$H_3$(Hz) | $C_4$— |
| AMM + MBP + bicelle ($D_{obs}$) 16.4 ± 1.1 | −10.8 ± 0.7 | −15.2 ± 0.7 | 13.3 ± 1.2 | 16.6 ± 1 |
| AMM + bicelle ($D_{free}$) 7.8 ± 0.5 | −3.5 ± 0.7 | −7.3 ± 0.7 | 9.2 ± 0.9 | 12.1 ± 0.7 |
| AMM − bound state ($D_{bound}$) 30.5 ± 3.0 | −22.6 ± 2.2 | −28.7 ± 2.2 | 20 ± 3.5 | 23.9 ± 2.9 |

In order to quantify the contribution from the AMM-free state, the same experiments were repeated under identical conditions in the absence of MBP. The differences in measured couplings between 25° C. and 39° C. are also shown field gradients. In all cases, bicelle alignment was monitored by 1$D^2H$ NMR quadrapolar splittings as a function of temperature with maximal alignment observed at 39° C. Spectra were acquired using normal hetero-nuclear ($^1H$—

$^{13}$C) single quantum coherence (HSQC) experiments modified so that $^{13}$C couplings were present in the direct proton dimension. Quadrature detection in the $t_1$ evolution period was accomplished using gradient coherence selection. For all experiments, 1024 points per scan, 16 scans per increment, 160 $t_1$ increments were acquired with a direct sweep width of 3000 Hz and an indirect sweep width of 9000 Hz. Using the same acquisition parameters, another identical HSQC experiment was acquird at a temperature of 25° C. where the bicelle medium is in an isotropic solution state.

Calculations of Dipolar Couplings and Order Tensors

Dipolar couplings were calculated as the difference between the oriented couplings ($^1J_{CH}+D_{CH}$) and the isotropic couplings ($^1J_{CH}$). In each case, couplings were extracted using a Bayesian time-domain NMR parameter estimation program Xrambo, using the method described (5). Typically, a 2D HSQC data set with the desired splittings in the direct dimension was transformed and phased to yield a 1024×256 real matrix. Single FID slices across the width of the resonance under investigation were analyzed independently. For every slice, the resulting frequency domain data were reverse Fourier transformed to generate a 1D time domain data set as input for Xrambo. The following model was used for the data. Each component of the doublet resulting from C—H couplings was given an identical linewidth and intensity, but an independent phase to circumvent any problems resulting from the presence of phase twist anomalies or dispersive contributions. Values for shifts, linewidths, phases and intensities were estimated and entered as starting parameters which were subsequently refined by Xrambo's Metropolis Monte Carlo method. This procedure was repeated for several indirect slices of the same doublet and the resulting rmsd across various slices was used as the uncertainty in measurement. The error analysis from this procedure was used to estimate the final precision of all measured residual dipolar couplings. The measured residual dipolar couplings and associated uncertainties along with AMM (alpha methyl mannose) input coordinates obtained from an MD simulation were then used as input to a singular value decomposition program for the determination of order tensor elements. (6)

MBP's Alignment Tensor

Figure 5:
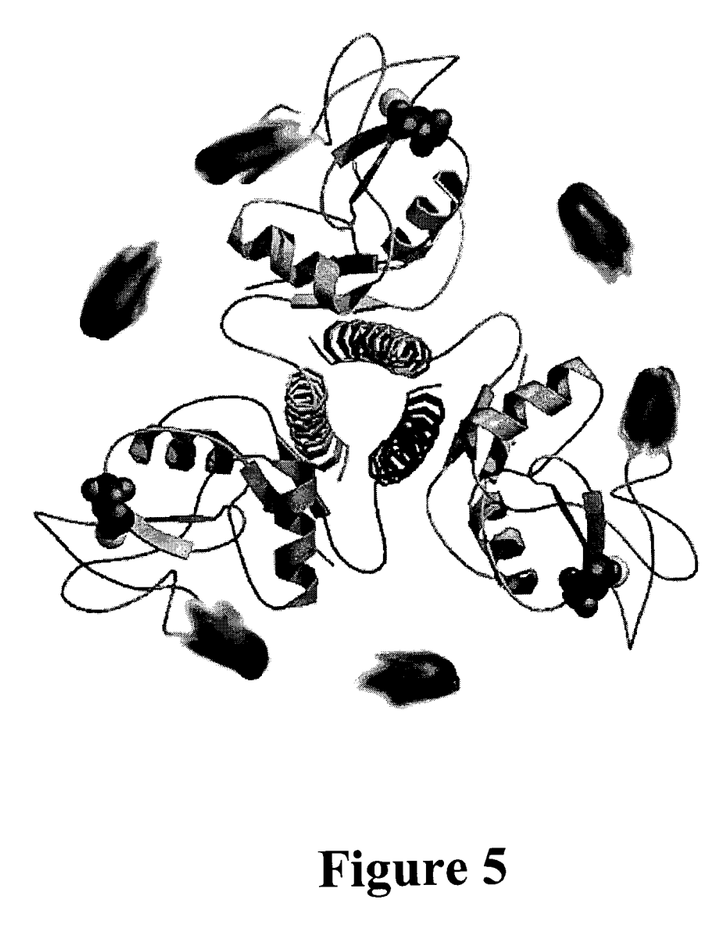

The form of MBP used in these studies is a homo-trimer with a 3-fold symmetry axis and three equivalent sugar binding sites related by the same symmetry operation as depicted in FIG. 5. The computed residual dipolar couplings originating from the AMM in the bound state ($D_{bound}$) will thus be an average over three orientations that are related by MBP's 3-fold symmetry axis. In the absence of any large conformational flexibility and mobility in the bound state, the order parameters determined from bound AMM ($S_{zzz}$=−0.0012(±0.00012)) will reflect MBP's order parameter. The fact that the principal order parameter is negative indicates that MBP's symmetry axis is, on average, perpendicular to the magnetic field and parallel with the normals of the bicelles in our medium (these order with their normals perpendicular to the magnetic field.

The Orientation of AMM Bound to MBP

Figure 6:
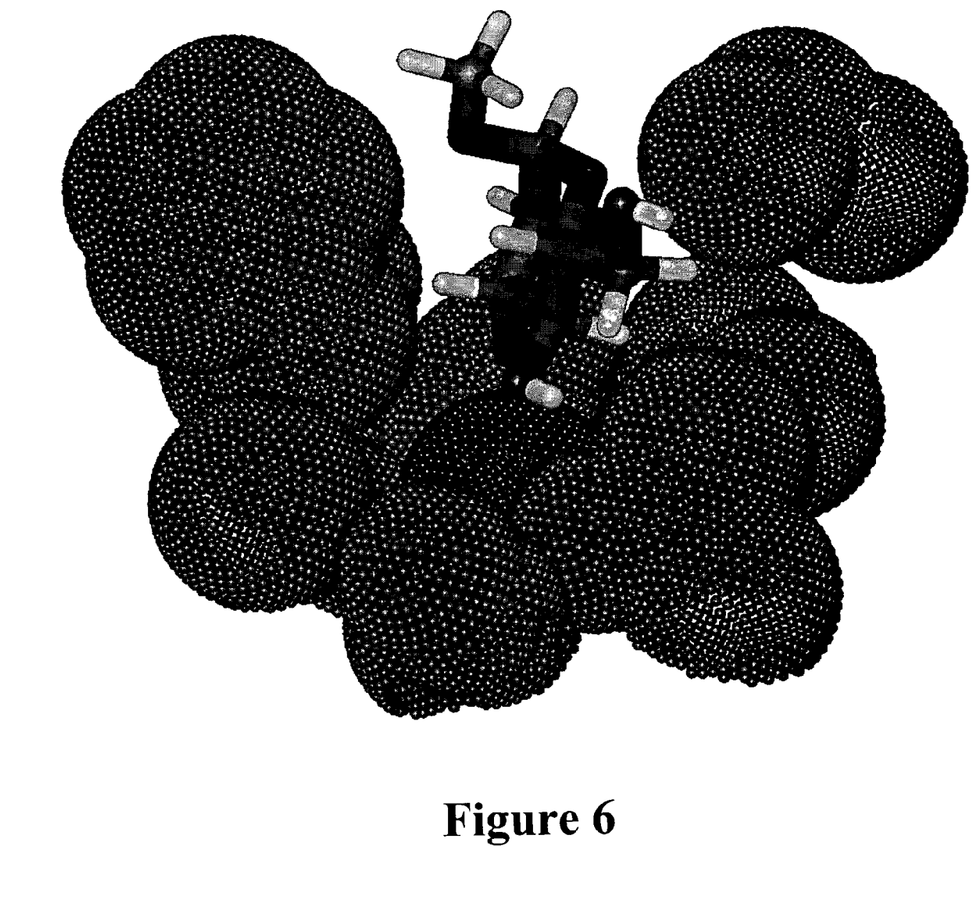
FIG. 6 shows a proposed mode of binding of AMM in MBP. The dark blue corresponds to $Ca^{2+}$, and the light blue represents residues in the binding pocket of MBP.
Figure 7:
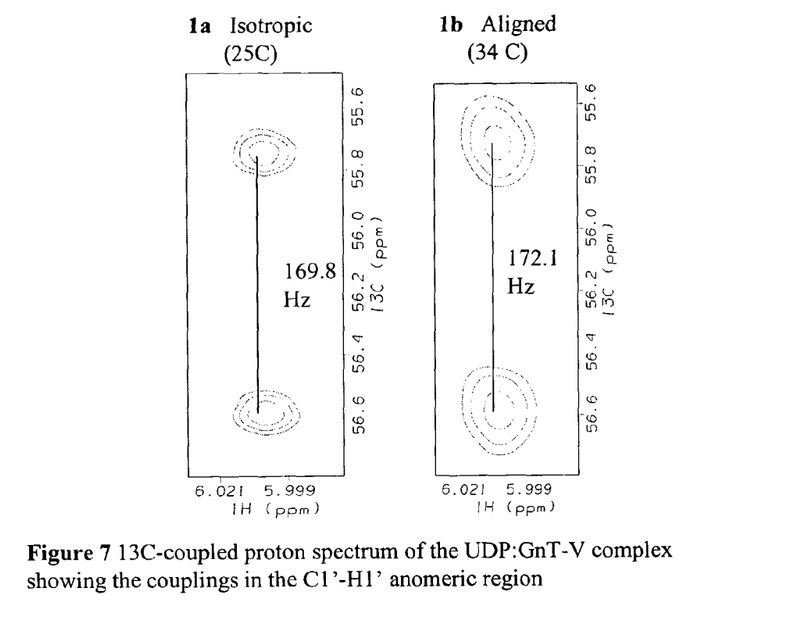
FIG. 7 depicts the $^{13}C$-coupled spectrum of the UDP:GnT-V complex showing the couplings of the C1'-H1' anomeric region.

In FIG. 6 we show a geometry of AMM in the binding site of MBP (KMB.pdb) that is consistent with our determined axis of symmetry. Using this refined structure, α-methyl marmose was docked to the binding calcium of the CRD of MBP. Orientational constraints required placing AMM's experimentally derived direction of highest order along MBP's 3-fold axis of symmetry. Subsequently, rotations around this axis and translation along x, y, and z, while maintaining a 2.6 Å distance from the $Ca^{2+}$ provided several possible orientations of AMM in MBP such as that depicted in FIG. 6. There is a single violation of allowed Van der Waals contacts (<2.5 Å) between HO-3 and Glu193 of MBP.

Molecular Dynamics Simulation

MD simulations were performed with AMBER 4.1 (7) employing the all-atom GLYCAM93 parameter set for oligosaccharides (8) on a 12 processor SGI Origin 2000 computer, AMM was solvated in an approximately 32 Å×32 Å×32 Å box of 466 TIP3P water molecules and was minimized by steepest descent energy minimization using a dielectric constant of 1.0 and a cut-off value for non-bonded pair interactions of 8.0 Å. Initial atomic velocities were assigned at 5K, and the simulation run at 300K at 1 atm. Selected torsions were extracted with the CARNAL module of AMBER 4.1 from the trajectories to determine a closely related family of the most populated structures.

Docking Studies

First approximations of AMM's position in MBP were done with MIDAS Plus. (9) Briefly, MBP with AMM modeled into the CRD were aligned with the helix parallel with the z-axis. A second AMM was matched and oriented according to the singular value decomposition analysis of the calculated dipolar couplings (a z-10°, y+40° rotation from the crystal structure). This was then translated in x, y, and z directions while limiting rotations to the z-axis only. Solutions that maintained the three and four OH groups 2.6–2.8 Å from the $Ca^{-2}$ responsible for binding and that minimized Van der Waals interaction with the protein were deemed plausible solutions.

Example 3 References (1) K. Drickamer (1989). Demonstration of carbohydrate-recognition activity in diverse proteins which share a common primary structure motif. *Biochem. Soc. Trans.* 17, 13–15.

(2) W. L. Weis, & K. Drickamer (1994). Trimeric structure of a C-type mannose-binding protein. *Structure*, 2, 1227–1240).

(3) B. J. Hare, C. R. Sanders, S. E. McIntyre & J. H. Prestegard (1993). Synthesis and characterization of a $^{13}$C-labeled alpha-mannosyl glycolipid analog from [$^{13}$C] glucose. *Chem. Phys. Lipids*, 66, 155–158.

(4) J. A. Losonczi & J. H. Prestegard (1998a). Improved dilute bicelle solutions for high-resolution NMR of biological macromolecules. *J. Biol. NMR*, 12, 447–451.

(5) M. Andrec & J. H. Prestgard (1998). Metropolis Monte Carlo implementation of Bayesian time-domain parameter estimation; application to coupling constant estimation from antiphase multiplets. *J. Magn. Reson.* 130, 217–232.

(6) J. A. Losonczi, M. Andrec, M. W. F. Fischer & J. H. Prestegard (1999). Order matrix analysis of residual dipolar couplings using singular value decomposition. *J. Magn. Reson.* 130, 217–232. 134, 334–342.

(7) U. C. Singh, P. K. Weiner, D. A. Pearlman, D. A. Case, G. Seibel J. C. Caldwell and P. Kollman, *Amber* 4.1 (University of California, San Francisco, USA).

(8) R. J. Woods, R. A. Dwek, C. J. Edge, B. Fraser-Reid (1995). Molecular mechanical and molecular dynamical simulations of plycoproteins and oligosaccharides. 1. GLYCAM_93 parameter development. *J. Phys. Chem.* 99, 3832–3846.

(9) T. E. Ferrin, C. C. Huang, L. E. Jarvis & R. Langridge, (1988). The MIDAS display System. *J. Mol. Graph.* 6, 13–27, 36–37.

(10) L. M. Bugayevskiy & J. P. Snyder, (1995). *Map Projections: A Reference Manual*, Taylor & Francis, London.

Example 4

Relative Orientation of Two Ligands in a Structurally Uncharacterized Protein GnT-V is a N-acetylglucosaminyl-transferase that catalyzes the transfer of N-acetylglucosamine (GlcNAc) from UDP-GlcNAc in beta(1,6)-linkage to the alpha(1,6)-linked mannose of N-linked oligosaccharides, resulting in highly branched beta-1,6 structures that have been linked to tumor growths and metastasis (Zhang et al., 1997). Development of specific inhibitors for this enzyme is therefore a potential source for novel therapeutics. Structural characterization of GnT-V might be useful for this purpose. However, GnT-V is of fairly high molecular weight (~95 kDa) and hence not amenable to structural study by NMR. It also represents a class of proteins for which no X-ray structures are currently available. Hence, it serves as an ideal protein target system for use of a dipolar coupling based strategy to determine relative orientation of two ligands on the protein surface, bypassing the need for knowledge of structure or resonance assignments for the protein. The two distinct natural sites for ligands in GnT-V, one for the donor UDP-GlcNAc and one for the acceptor, a mannose terminated oligosaccharide, provide a good test-bed for our strategy.

We present the binding of UDP to GnT-V, a competitive inhibitor of GnT-V with a binding constant similar to that of UDP-GlcNAc (1.1 mM), as an example of orientation determination for one ligand. The binding of the acceptor can be studied in a similar manner Preparation of GnT-V The soluble form of recombinant human GnT-V was expressed in CHO cells and then purified using a combination of a phenyl sepharose column, a copper chelating column and an SP sepharose column (Zhang et al.). The purified material was then dialysed versus 50 mM MES buffer, pH 6.5 containing 100 mM NaCl for further use in NMR experiments.

Measurement of Resdiual Dipolar Couplings in UDP Complexed to GnT-V

A sample of UDP (Sigma Chemicals) complexed with GnT-V in 50 mM MES buffer, pH 6.5, 100 mM NaCl was prepared in a dilute bicelle medium (10%). The concentration of UDP in the sample was 1.75 mM, while that of the protein was 0.05 mM. $^1$H—$^{13}$C spectra (at natural abundance for $^{13}$C) were collected for this sample at temperatures of 25° C. and 34° C. (FIGS. 1a and 1b). to provide measurements in isotropic and aligned enviromnents respectively. The spectra were acquired with splitting in the $^{13}$C dimension. One-bond $^1$H—$^{13}$C couplings were measured from these splittings. Residual dipolar contributions for individual C—H bond vectors were calculated from the differences in couplings at 25° C. (isotropic) and 34° C. (aligned) and are shown in Table 3.

In order to quantify the contribution from the UDP-free state, the same experiments were repeated under identical conditions in the absence of GnT-V. The differences in measured couplings between 25° C. and 34° C. are also shown in Table 3 ($D_{free}$). The residual dipolar contributions from the UDP in the bound state ($D_{bound}$) were then calculated from a population weighted average from the free ($N_{free}$) and bound ($N_{bound}$) states—

$$D_{obs}=N_{free}D_{free}+N_{bound}D_{bound}$$

where $D_{obs}$ is the observed residual dipolar coupling measured in the UDP/GnT-V complex. The fraction of UDP free and bound ($N_{free}$ and $N_{bound}$) were calculated from the known binding constant of 1.1 mM for UDP and known protein-ligand concentrations. Residual dipolar couplings from the bound state ($D_{bound}$) are shown in Table 3.

TABLE 3

| Data Set | C1'–H1' (Hz) | C2'—H2'(Hz) | C3'—H3'(Hz) | C4'—H4'(Hz) | C5'—H5'(Hz) |
| --- | --- | --- | --- | --- | --- |
| UDP + GnT-V + bicelle ($D_{obs}$) | 2.3 ± 0.3 | −0.6 ± 0.3 | −0.6 ± 0.3 | 0.9 ± 0.3 | 0.7 ± 0.3 |
| UDP + bicelle ($D_{free}$) | 3.1 ± 0.3 | −0.4 ± 0.3 | −0.9 ± 0.3 | 0.4 ± 0.3 | 0.4 ± 0.3 |
| UDP – bound state($D_{bound}$) | −27.8 ± 1.2 | −5.2 ± 1.2 | 13.4 ± 1.2 | 19.3 ± 1.2 | 10.3 ± 1.2 |

Order Tensor Calculation in UDP

Figure 8:
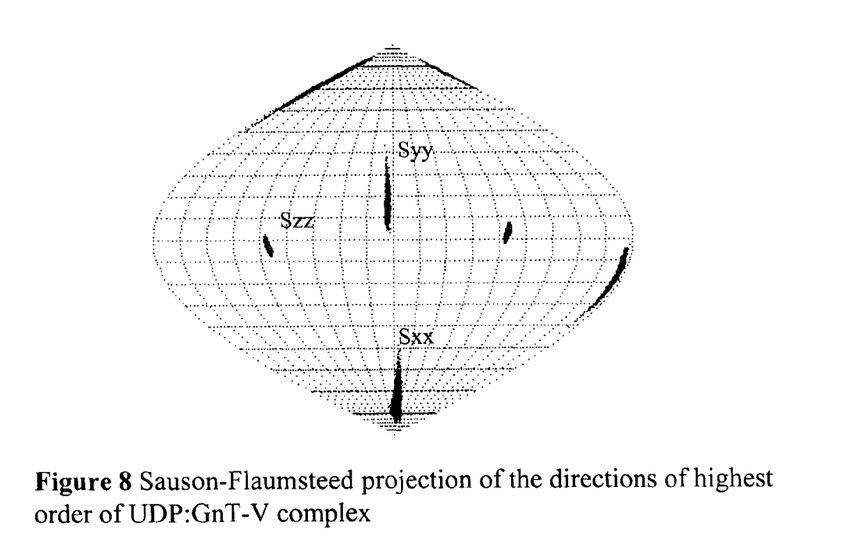
FIG. 8 is a Sauson-Flaumsteed projection of the directions of highest order of the UDP:GnT-V complex.

Using the five residual dipolar couplings calculated above for the bound-state UDP and structural coordinates for UDP obtained from the X-ray crystal structure of a human UDP-Galactose 4-Epimerase that contains UDP-GlcNAc in its active site (Thoden et al., 2001), five elements of an order matrix were determined using a singular value decomposition method (Losonczi et al., 1998). The directions of the principal axes of the order tensor are depicted in FIG. 8 using a Sauson-Flaumsteed projection (Ref.).

Relative Orientation of Two Fragments

Similar residual dipolar coupling measurements have been carried out on a trisaccharide acceptor and are not shown here. However, assuming the dipolar measurements of the acceptor are available, an order tensor for the acceptor can be calculated in a similar manner as above. Since the ordering of the protein in a liquid crystallline bicelle media dictates the order of its bound ligands, the relative orientation of the bound acceptor with respect to bound UDP can then be determined by rotating the molecular frame of the acceptor, such that its ordering frame as determined from the order tensor matches the ordering frame of UDP.

References for Example 4

(1) Bugayevskiy, L. M. and Snyder, J. P. (1995) Map Projections: A Reference Manual, Taylor & Francis, London.

(2) Losonczi, J. A.; Andrec, M.; Fischer, M. W. F. and Prestegard, J. H. (1999) *J. Magn. Reson.* 134, 334–342.
(3) Thoden, J. B.; Wohlers, T. M.; Fridovich-Keil, J. L. and Holden, H. M. (2001) *J. Biol. Chem.* 276, 15131.
(4) Zhang, N.; Peng, K. C.; Chen L.; Peutt, D. and Pierce, M. (1997) *J. Biol. Chem.* 272, 4225.

CONCLUSION

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for improving the binding affinity of a ligand for a biological target comprising:
    a) preparing first NMR spectra of a first complex comprising the biological target and a paramagnetically labeled derivative of a first ligand to define a paramagnetic zone;
    b) preparing second NMR spectra of a second complex comprising the biological target and a second ligand;
    c) analyzing the spectra to determine whether the second ligand binds to the biological target within the paramagnetic zone of the paramagnetically labeled derivative;
    d) deducing a relative three-dimensional orientation of the first and second ligands when bound to the biological target;
    e) deducing a distance of separation of the first and second ligands when bound to the biological target; and
    f) selecting or preparing a compound that contains the first and second ligands substantially in the relative orientation and distance.

2. The method of claim 1 wherein step (c) is performed by:
    a) identifying peaks on the first NMR spectra that are perturbed by the paramagnetic label; and
    b) determining whether the second ligand perturbs peaks on the second NMR spectra that are also perturbed by the paramagnetic label.

3. The method of claim 1 wherein the first complex further comprises the second ligand, and step (c) is performed by determining whether the paramagnetically labeled derivative of the first ligand perturbs peaks associated with the second ligand.

4. The method of claim 3 further comprising, before step (c), preparing third NMR spectra of a mixture of the paramagnetically labeled derivative of the first ligand and the second ligand in the absence of the biological target.

5. The method of claim 1 wherein the distance of separation is determined as a function of the loss of intensity for NMR resonances from the second ligand.

6. The method of claim 1 wherein the three dimensional orientation is deduced by producing a field ordered state in a medium comprising the biological target, the first ligand, and the second ligand, and analyzing dipolar couplings within the first and second ligands.

7. The method of claim 6 wherein the field ordered state is produced by an aqueous dispersion of lipid bicelles having complementary charges to the biological target.

8. The method of claim 6 wherein the field ordered state is produced by an aqueous dispersion of bacteriophage having a domain of the biological target in the outer coat.

9. The method of claim 1 wherein the paramagnetic label is a nitroxide or metal chelate.

10. The method of claim 1 wherein the first and second NMR spectra are two dimensional heteronuclear single quantum coherence spectra.

11. The method of claim 1 wherein the biological target is isotopically labeled.

12. The method of claim 1 wherein the biological target is a protein, and NMR resonances from the protein are not assigned to a sequence of the protein.

13. The method of claim 1 wherein the biological target is a protein, and the three dimensional conformation of the protein is unknown.

14. The method of claim 1 wherein the first ligand is an oligosaccharide, and the biological target is a protein.

15. The method of claim 1 wherein the second complex comprises the first ligand, or a paramagnetically labeled derivative thereof.

16. A method for improving the binding affinity of ligands for biological targets comprising:
    a) preparing first NMR spectra of a first complex comprising a biological target, a paramagnetically labeled derivative of a first ligand, and a second ligand;
    b) preparing second NMR spectra of a second complex comprising the biological target and either the second ligand or the paramagnetically labeled derivative of the first ligand;
    c) preparing third NMR spectra of a mixture of the paramagnetically labeled derivative of the first ligand and the second ligand in the absence of the biological target;
    d) analyzing the spectra to determine whether the paramagnetically labeled derivative of the first ligand perturbs peaks associated with the second ligand;
    e) deducing a relative three-dimensional orientation of the first and second ligands when bound to the biological target;
    f) deducing a distance of separation of the first and second ligands when bound to the biological target; and
    g) selecting or preparing a compound that contains the first and second ligands substantially in the relative orientation and distance.

17. The method of claim 16 further comprising:
    a) deducing from the NMR spectra the distance between the first and second ligands when bound to the biological target;
    b) deducing from the NMR spectra the relative three dimensional orientation of the first and second ligand when bound to the biological target; and
    c) selecting or preparing a hybrid ligand that contains the first and second ligands covalently linked substantially at the bond distance and relative orientation deduced in steps (a) and (b).

* * * * *